(12) United States Patent
Russell et al.

(10) Patent No.: US 10,772,516 B2
(45) Date of Patent: Sep. 15, 2020

(54) OPPOSING ACCELEROMETERS FOR A HEART RATE MONITOR

(71) Applicant: KONINKLIJKE PHILIPS N.V., Eindhoven (NL)

(72) Inventors: James Knox Russell, Seattle, WA (US); Haris Duric, Bothell, WA (US); Chenguang Liu, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 262 days.

(21) Appl. No.: 15/104,258

(22) PCT Filed: Dec. 10, 2014

(86) PCT No.: PCT/IB2014/066745
§ 371 (c)(1),
(2) Date: Jun. 14, 2016

(87) PCT Pub. No.: WO2015/092618
PCT Pub. Date: Jun. 25, 2015

(65) Prior Publication Data
US 2016/0317040 A1   Nov. 3, 2016

Related U.S. Application Data

(60) Provisional application No. 61/918,095, filed on Dec. 19, 2013.

(51) Int. Cl.
*A61B 5/024* (2006.01)
*A61B 5/00* (2006.01)
(Continued)

(52) U.S. Cl.
CPC ............ *A61B 5/024* (2013.01); *A61B 5/0245* (2013.01); *A61B 5/0402* (2013.01); *A61B 5/11* (2013.01);
(Continued)

(58) Field of Classification Search
CPC ........ A61B 5/024–0255; A61B 5/6819; A61B 5/7214; A61B 5/11; A61B 5/1102; A61B 2562/0219
See application file for complete search history.

(56) References Cited

U.S. PATENT DOCUMENTS 6,431,705 B1 *   8/2002   Linden ................... G02C 11/00
                                                          351/158
6,941,775 B2 *   9/2005   Sharma .............. A41D 13/1281
                                                            2/902
(Continued)

FOREIGN PATENT DOCUMENTS

EP   2229880 A1   9/2010
JP   H07116138 A   5/1995
(Continued)

OTHER PUBLICATIONS

Dresher (Wearable Forehead Pulse Oximetry: Minimization of Motion and Pressure Artifacts, 2006, Thesis, Worcester Polytechnic Institute).*

*Primary Examiner* — Meredith Weare

(57) ABSTRACT

A heart rate monitor (40) for detecting a pulse of a person (10) employs a platform (43), a plurality of multi-axis accelerometers (41R, 41L) and a pulse detector (44). The multi-axis accelerometers (41R, 41L) are adjoined to the platform (43) to generate differential mode signals ($A_{ZR}$, $A_{ZL}$) indicative of a sensing by the accelerometers (41) of physiological motion (12) of the person (10) relative to acceleration sensing axes (42R, 42L) and to generate common mode signals ($A_{XR}$, $A_{XL}$, $A_{YR}$, $A_{YL}$) indicative of a sensing by the accelerometers (41R, 41L) of extraneous motion by the person (10) relative to the acceleration sensing axes (42R, 42L). The pulse detector (44) is operably connected to the multi-axis accelerometers (41R, 41L) to generate a pulse signal (PS)as a function of a vertical (Continued)

alignment of the acceleration sensing axes (42R, 42L) combining the differential mode signals ($A_{ZR}$, $A_{ZL}$) and cancelling the common mode signals ($A_{XR}$, $A_{XL}$, $A_{YR}$, $A_{YL}$).

13 Claims, 5 Drawing Sheets

(51) Int. Cl.
  *A61B 5/11* (2006.01)
  *A61B 5/0245* (2006.01)
  *A61B 5/0402* (2006.01)
  *A61N 1/39* (2006.01)
(52) U.S. Cl.
  CPC .......... *A61B 5/6803* (2013.01); *A61B 5/6819* (2013.01); *A61B 5/6838* (2013.01); *A61B 5/7214* (2013.01); *A61B 5/742* (2013.01); *A61N 1/3925* (2013.01); *A61B 2562/0219* (2013.01)

(56) References Cited

U.S. PATENT DOCUMENTS

| | | | |
|---|---|---|---|
| 6,997,882 B1* | 2/2006 | Parker | A61B 5/08 600/301 |
| 2003/0097158 A1* | 5/2003 | Belalcazar | A61N 1/3702 607/32 |
| 2004/0215244 A1 | 10/2004 | Marcovecchio et al. | |
| 2008/0214963 A1* | 9/2008 | Guillemaud | A61B 5/0205 600/595 |
| 2008/0312709 A1 | 12/2008 | Volpe et al. | |
| 2011/0066042 A1* | 3/2011 | Pandia | A61B 5/029 600/484 |
| 2012/0022339 A1* | 1/2012 | Joo | A61B 5/0535 600/301 |
| 2012/0065524 A1* | 3/2012 | Morren | A61B 5/1102 600/484 |
| 2012/0136573 A1 | 5/2012 | Janardhanan et al. | |
| 2012/0197353 A1 | 8/2012 | Donnelly et al. | |
| 2012/0302900 A1 | 11/2012 | Yin et al. | |
| 2013/0039241 A1* | 2/2013 | Ruvalcaba | H04W 52/0241 370/311 |
| 2013/0013342 A1 | 5/2013 | Donaldson | |
| 2013/0131525 A1 | 5/2013 | Yin et al. | |
| 2013/0231711 A1 | 9/2013 | Kaib | |

FOREIGN PATENT DOCUMENTS

| | | | | |
|---|---|---|---|---|
| JP | 2003047600 A | 2/2003 | | |
| JP | 2014516233 | 7/2014 | | |
| WO | WO-2012017355 A1 * | 2/2012 | ......... | A61B 5/02055 |
| WO | 2012125135 A1 | 9/2012 | | |
| WO | 2012170550 A1 | 12/2012 | | |

* cited by examiner

US 10,772,516 B2

OPPOSING ACCELEROMETERS FOR A HEART RATE MONITOR

CROSS-REFERENCE TO PRIOR APPLICATIONS

This application is the U.S. National Phase application under 35 U.S.C. § 371 of International Application No. PCT/IB2014/066745, filed on Dec. 10, 2014, which claims the benefit of U.S. Provisional Patent Application No. 61/918,095 filed on Dec. 19, 2013. These applications are hereby incorporated by reference herein.

The present invention generally relates to a heart rate monitor employing an accelerometer as a basis for detecting a pulse of a patient. The present invention specifically relates to a heart rate monitor employing multi-axis accelerometers in an angular orientation that facilitates a distinction of a pulse of a patient from motion artifacts derived from extraneous motion of the patient.

Heart rate monitors as known in the art execute a measurement of a patient's heart rate in real time. In particular, for emergency care directed to triage and guidance of cardiac therapy, heart rate monitors are designed to be simple to use, noninvasive and reliable for pulse detection purposes. To this end, as shown in FIG. 1, current heart rate monitors are known to employ a multi-axis (XYZ) accelerometer 20 strapped to a chest of a person 10 over any of several easily accessible arteries of person 10 to thereby sense undulating physiological motion 12 of person 10 generated by a circulatory system 11 of person 10 as a basis for detecting the pulse of person 10. However, XYZ axes 21 of accelerometer 20 experience acceleration derived from a totality of motion of person 10. Thus, while pulses of person 10 produce measurable physiological motion 12, motion sources extrinsic to person 10 may produce larger motion artifacts from larger undulating extraneous motion 13 that conceals physiological motion 12 of person 10 (e.g., cardiopulmonary resuscitation ("CPR") efforts on person 10, transportation/movement of person 10, etc.). Consequently, the motion artifacts limit the applicability of accelerometer 20 as strapped to the chest of person 10 for pulse detection.

To overcome the drawback of accelerometer 20, the present invention as shown in FIG. 2 involves a placement of two (2) multi-axis (XYZ) accelerometers 20R and 20L on a body surface of person 10 at an angular orientation whereby respective XYZ axes 21R and 21L of accelerometers 20R and 20L individually sense physiological motions 12R and 12L generated by circulatory system 11 and equally sense motion artifacts generated from extraneous motion 13. Specifically, respective vertical axes $Z_R$ and $Z_L$ are normal to the body surface of person 10 to individually experience acceleration primarily, if not entirely, derived from respective physiological motions 12R and 12L. Conversely, respective longitudinal axes $X_R$ and $X_L$ and respective lateral axes $Y_R$ and $Y_L$ are parallel to the body surface of patient to commonly experience acceleration primarily, if not entirely, derived from extraneous motion 13. For example, as will be further described herein, accelerometers 20R and 20L may be mounted to a nose 15 of person 10 as shown in FIG. 2 or strapped to a head 16 of person 10 as shown in FIG. 2 to individually sense respective physiological motion 12R and 12L and to commonly sense extraneous motion 13. Knowledge of the angular orientation of accelerometers 20R and 20L facilitates a mathematical rotation of XYZ axes 21R and 21L of accelerometers 20R and 20L to a baseline XYZ axes 21B that permits cancellation of extrinsic extraneous motion 13 and reinforcement of physiological motion 12 due to the difference in the orientation of the forces exerted by the totality of motion sensed by accelerometers 20R and 20L.

One form of the present invention is a method for pulse detection of a person by a heart rate monitor including a plurality of multi-axis accelerometers. The method involves the accelerometers generating differential mode signals indicative of a sensing by the accelerometer of physiological motion of the person relative to acceleration sensing axes, and the accelerometers generating common mode signals indicative of a sensing by the accelerometers of extraneous motion by the person relative to the acceleration sensing axes. The method further involves the heart rate monitor generating a pulse signal as a function of a vertical alignment of the acceleration sensing axes combining the differential mode signals and cancelling the common mode signals.

For purposes of the present invention, the term "physiological motion" is broadly defined herein as any motion of a body or a portion thereof generated by a circulatory system of the body to any degree, whether natural (e.g., a pulse from a self-regulated heartbeat) or induced (e.g., a pulse induced by a CPR chest compression), and the term "extraneous motion" is broadly defined herein as any motion of a body or a portion thereof resulting from an application of a force from a source external to the body.

A second form of the present invention is heart rate monitor for detecting a pulse of a person that employs a platform, a plurality of multi-axis accelerometers and a pulse detector. In operation, the multi-axis accelerometers are adjoined to the platform to generate differential mode signals indicative of a sensing by the accelerometers of physiological motion of the person relative to acceleration sensing axes and to generate common mode signals indicative of a sensing by the accelerometers of extraneous motion by the person relative to the acceleration sensing axes The pulse detector generates a pulse signal as a function of a vertical alignment of the acceleration sensing axes combining the differential mode signals and cancelling the common mode signals.

A third form of the invention is a cardiac therapy system (e.g., an automated external defibrillator or an advanced life support defibrillator/monitor) employing the aforementioned heart rate monitor and a pulse monitor responsive to the pulse signal to monitor the pulse of the patient.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

To facilitate an understanding of the present invention, exemplary embodiments of a heartbeat monitor of the present invention will be provided herein directed to a stand-alone monitor and an incorporation of the heartbeat monitor of the present invention into a cardiac therapy device (e.g., an automated external defibrillator or an advanced life support).

Figure 3:
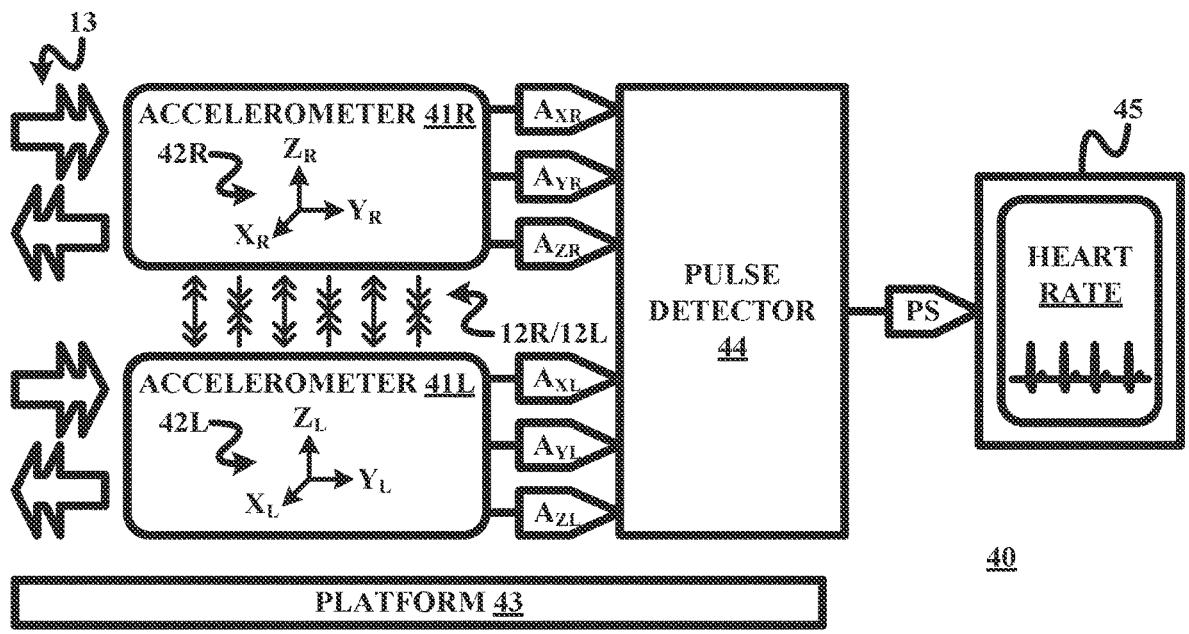
FIG. 3 illustrates an exemplary embodiment of a heart rate monitor in accordance with the present invention.

Referring to FIG. 3, a heartbeat monitor 40 of the present invention employs a pair of multi-axis (XYZ) accelerometers 41R and 41L, a platform 43, a pulse detector 44 and a display 45.

Accelerometer 41R structurally configured as known in the art for generating a longitudinal acceleration sensing signal $A_{XR}$, a lateral acceleration sensing signal $A_{YR}$, and a vertical acceleration sensing signal $A_{ZR}$ responsive to a sensing of motion force(s) acting upon an XYZ axes 42R.

Accelerometer 41L structurally configured as known in the art for generating a longitudinal acceleration sensing signal $A_{XL}$, a lateral acceleration sensing signal $A_{YL}$, and a vertical acceleration sensing signal $A_{ZL}$ responsive to a sensing of motion force(s) acting upon an XYZ axes 42L.

In practice, heartbeat monitor 40 may employ additional accelerometers 41.

Also in practice, heartbeat monitor 40 may alternatively or concurrently employ two (2) or more multi-axis (XY) accelerometers, and may alternatively or concurrently employ two (2) or more groupings of single-axis (X) accelerometers serving as multi-axis accelerometers.

Platform 43 is structurally configured in accordance with the present invention for positioning respective vertical axes $Z_R$ and $Z_L$ of accelerometers 41R and 41L normal to body surface of a person, and for positioning respective longitudinal axes $X_R$ and $X_L$ and respective lateral axes $Y_R$ and $Y_L$ of accelerometers 41R and 41L parallel to the body surface of the person. As exemplary shown in FIG. 2, platform 43 is further structurally configured to angularly orientate XYZ axes 42R and XYZ axes 42L whereby respective vertical axes $Z_R$ and $Z_L$ are normal to the body surface of the person to individually experience acceleration primarily, if not entirely, derived from respective physiological motion 12R and 12L, and whereby respective longitudinal axes $X_R$ and $X_L$ and respective lateral axes $Y_R$ and $Y_L$ are parallel to the body surface of patient to commonly experience acceleration primarily, if not entirely, derived from extraneous motion 13. Consequently, for purposes of the present invention, vertical acceleration sensing signal $A_{ZR}$ and vertical acceleration sensing signal $A_{ZL}$ are deemed differential mode signals while longitudinal acceleration sensing signal $A_{XR}$, lateral acceleration sensing signal $A_{YR}$, longitudinal acceleration sensing signal $A_{XL}$, and lateral acceleration sensing signal $A_{YL}$ are deemed common mode signals.

Figure 5:
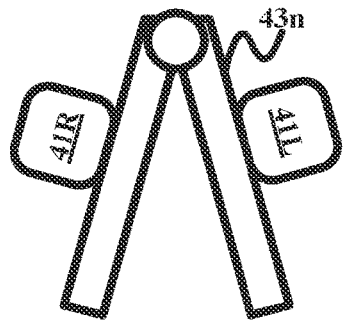
FIG. 5 illustrates an exemplary embodiment of a nose clip in accordance with the present invention.

One embodiment of platform 43 is a hinged or jointed nose clip 43n as shown in FIG. 5, which is structurally configured to flexibly affix accelerometers 41R and 41L to opposite right and left sides of a bridge of a nose of the person whereby the underlying nasal bone will rigidly maintain the angular orientation of accelerometers 41R and 41L with respect to one another and the nose of the person. More particularly, dorsal nasal arteries of the person are intimately connected via the opthalmic artery to the internal carotid, and thus to the blood supply of the brain. A pulse at the bridge of the nose is preserved, if it is preserved anywhere in physiological distress, and in particular it is not subject to peripheral shutdown common in patients needing emergency care. Consequently, respective vertical axes $Z_R$ and $Z_L$ (FIG. 3) of accelerometers 41R and 41L will experience physiological motion from pulsation of the dorsal nasal arteries primarily normal to the plane of the temporal bone, and respective longitudinal axes $X_R$ and $X_L$ and respective lateral axes $Y_R$ and $Y_L$ will experience motion artifacts of the nose of the person primarily along the plane of the nasal bone.

Figure 7:
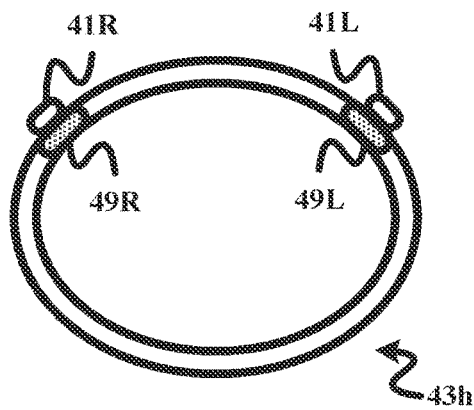
FIG. 7 illustrates an exemplary embodiment of a headband/head strap in accordance with the present invention.

Another embodiment of platform 43 is a headband/head strap 43h as shown in FIG. 7, which is structurally configured with hardened surfaces 49R and 49L to respectively affix accelerometers 41R and 41L to opposite right and left temples of the person whereby surfaces 49R and 49L will rigidly maintain the angular orientation of accelerometers 41R and 41L with respect to one another and the temples of the person. As with the dorsal nasal arties, the temporal arteries is substantially preserved and not subject to peripheral shutdown common in patients needing emergency care. Consequently, respective vertical axes $Z_R$ and $Z_L$ (FIG. 3) of accelerometers 41R and 41L will experience physiological motion from pulsation of the temporal arteries primarily normal to the plane of the nasal bone, and respective longitudinal axes $X_R$ and $X_L$ and respective lateral axes $Y_R$ and $Y_L$ will experience motion artifacts of the temples of the person primarily along the plane of the temples.

Figure 4:
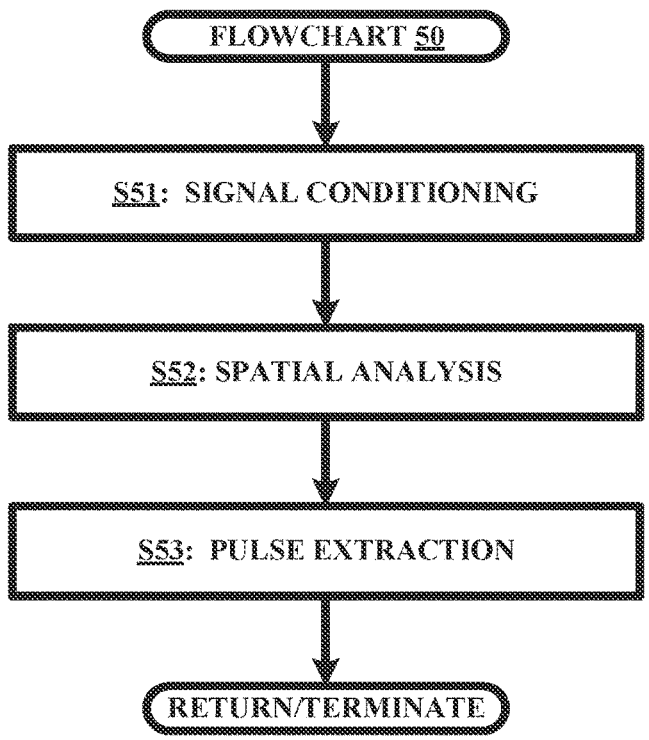
FIG. 4 illustrates a flowchart representative of an exemplary embodiment of pulse detection method in accordance with the present invention.

Referring back to FIG. 3, pulse detector 44 is structurally configured with hardware, software, firmware and/or circuitry for executing a pulse detection method of the present invention as represented by a flowchart 50 shown in FIG. 4.

A stage S51 of flowchart 50 encompasses pulse detector 44 implementing technique(s) for conditioning acceleration sensing signals $X_R$, $Y_R$, $Z_R$, $X_L$, $Y_L$ and $Z_L$ as needed for accelerometers 41R and 41L. Examples of the known signal conditioning include, but are not limited to, signal amplification and analog-to-digital conversion.

Figure 1:
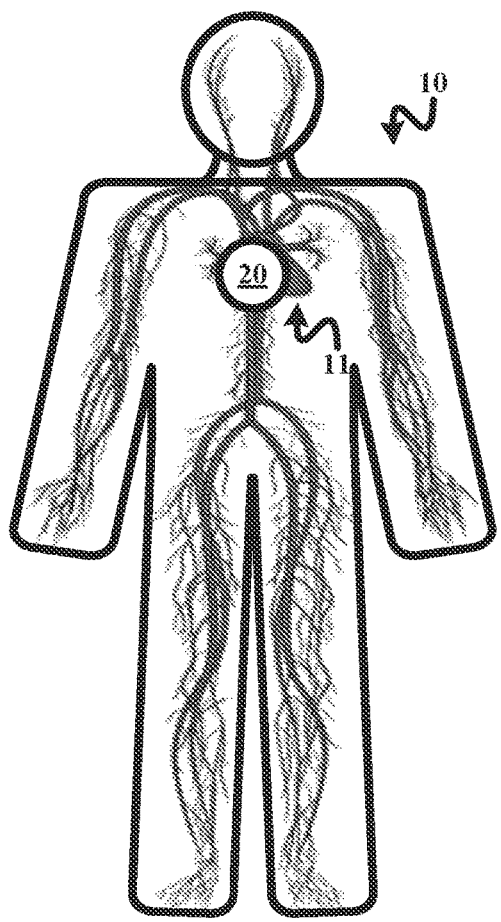
FIG. 1 illustrates an exemplary placement of a multi-axis accelerometer on a body surface of a patient as known in the art.
Figure 1:
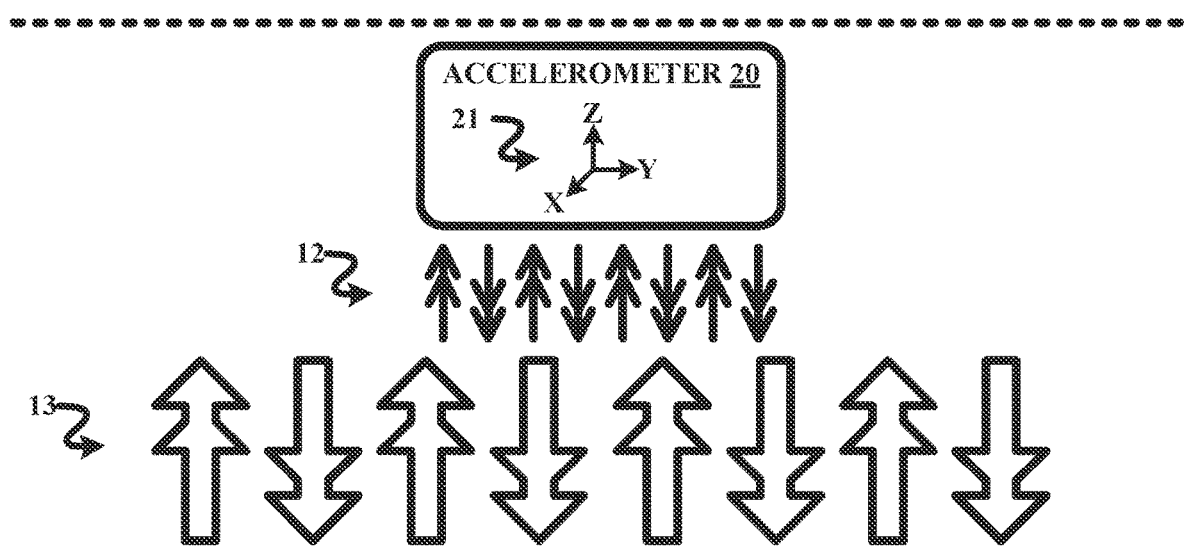
Figure 2:
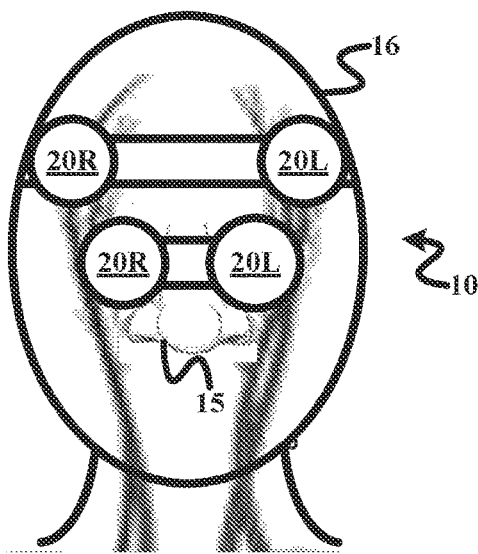
FIG. 2 illustrates exemplary placements of two (2) multi-axis accelerometers on a body surface of a patient in accordance with the present invention.
Figure 2:
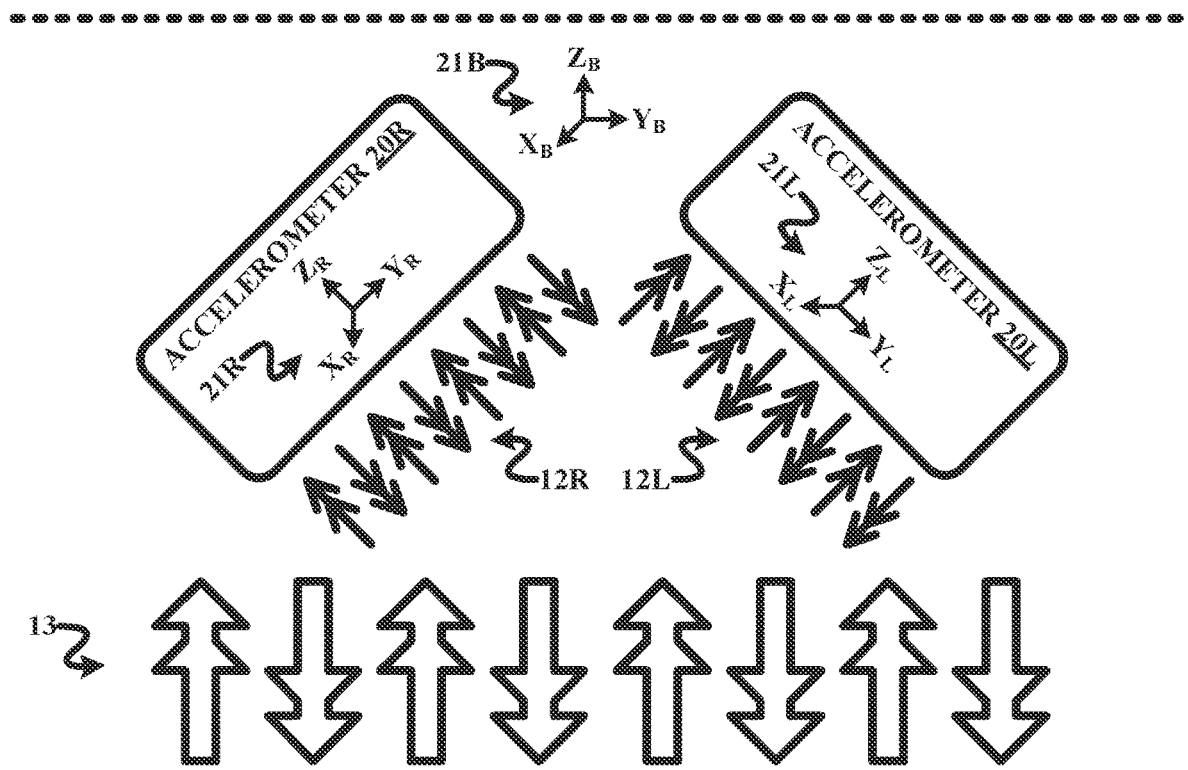

A stage S52 of flowchart 50 encompasses pulse detector 44 implementing technique(s) for spatially analyzing an angular orientation of XYZ axes 42R and 42L relative to a baseline axes (e.g., one of XYZ axes 42R or XYZ axes 42L, or a distinct baseline XYZ axes such as 21B shown in FIG. 2). In one embodiment, gravity acceleration vectors of XYZ axes 42R and 42L are used as excitation field to determine a tile angle between accelerometers 41R and 41L or to a distinct baselines axes (e.g., baseline XYZX axes 21B shown in FIG. 2) to facilitate a mathematical rotation of XYZ axes 42R and 42L in all three dimensions to align vertical axes $Z_R$ and $Z_L$ whereby individual physiological motion vectors, common motion artifact vector and the gravity acceleration vectors are identifiable by pulse detector 44.

A stage S53 of flowchart 50 encompasses pulse detector 44 implementing technique(s) for extracting the physiological motion vectors to communicate a pulse signal PS (FIG. 3) to display 45. Generally, pulse detector 44 extracts corresponding physiological motion vectors, motion artifact vectors and the gravity vectors from vertically aligned XYZ axes 42R and 42L by combining the differential mode signals $A_{ZR}$ and $A_{ZL}$ and cancelling common mode signals $A_{XR}$, $A_{XL}$, $A_{YR}$ and $A_{YL}$.

Specifically for combining/cancelling the signals, particularly when vertical axes $Z_R$ and $Z_L$ are not pointed in opposite directions on the body surface of the person, advanced signal processing methods known in the art (e.g., Principal Component Analysis (PCA) or Independent Component Analysis (ICA)) may be utilized to extract the physiological motion vectors from vertically aligned XYZ axes 42R and 42L. For example, PCA may sort the signal components from the biggest to the smallest. The gravity acceleration vectors and common motion artifact vectors are bigger signals than the physiological motion vectors, and the gravity acceleration vectors and the common motion artifact vectors identified by PCA and removed. By further example, ICA may extract the independent components if they are linearly combined. Since the physiological motion vectors, the gravity acceleration vectors and the common motion artifact vectors are independent to each other and the recordings by accelerometers 41R and 41L are a linear sum, the physiological motion vectors may be identified from the ICA results. Furthermore, since the pulses from both sides of the bridge of nose are correlated and synchronized, the extracted physiological motion vectors by ICA should by default be the sum of the blood pulses recorded by the two accelerometers 41R and 41L.

Referring back to FIG. 3, in practice, pulse detector 44 may employ one or more modules with each module being affixed to platform 43, within a stand-alone housing or incorporated within display 45.

Figure 6:
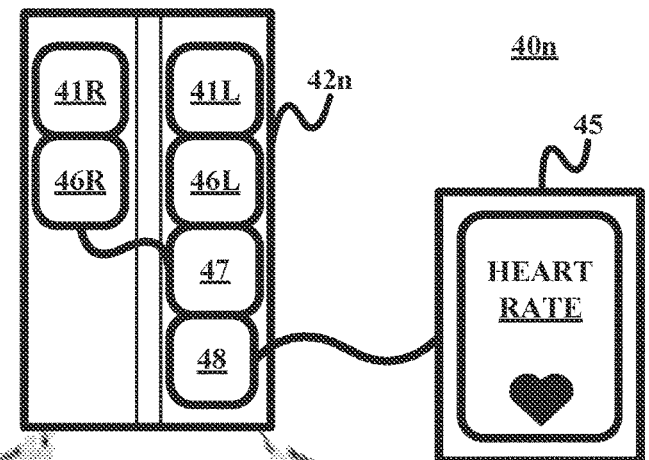
FIG. 6 illustrates an exemplary embodiment of a heart rate monitor incorporating the nose clip shown in FIG. 5 in accordance with the present invention.
Figure 8:
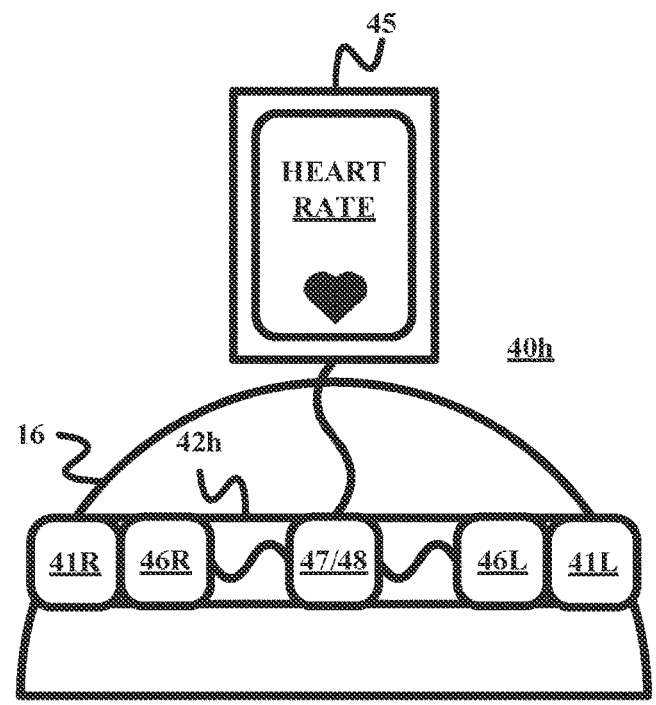
FIG. 8 illustrates an exemplary embodiment of a heart rate monitor incorporating the headband/head strap shown in FIG. 7 in accordance with the present invention.

For example, as respectively shown for heartbeat monitors 40n and 40h in FIGS. 6 and 8, pulse detector 44 employs modules in the form of signal conditioners 46R and 46L, a spatial analyzer 47 and a pulse extractor 48 affixed to nose clip 45n and headband/head strap 45h.

Referring back to FIG. 3, display 45 is structurally configured as known in the art for visually displaying pulse signal PS or visual indications thereof and optionally providing audio information related to pulse signal PS. For example, as shown, display 45 may provide a heartbeat readout of pulse signal PS and provide a pulsating heart as an indication of pulse signal PS.

In practice, display 45 may be affixed to platform 43, within a stand-alone housing or incorporated within a cardiac therapy device. For example, as shown in as respectively shown for heartbeat monitors 40n and 40h in FIGS. 6 and 8, display 45 is provided in stand-alone housing.

Figure 9:
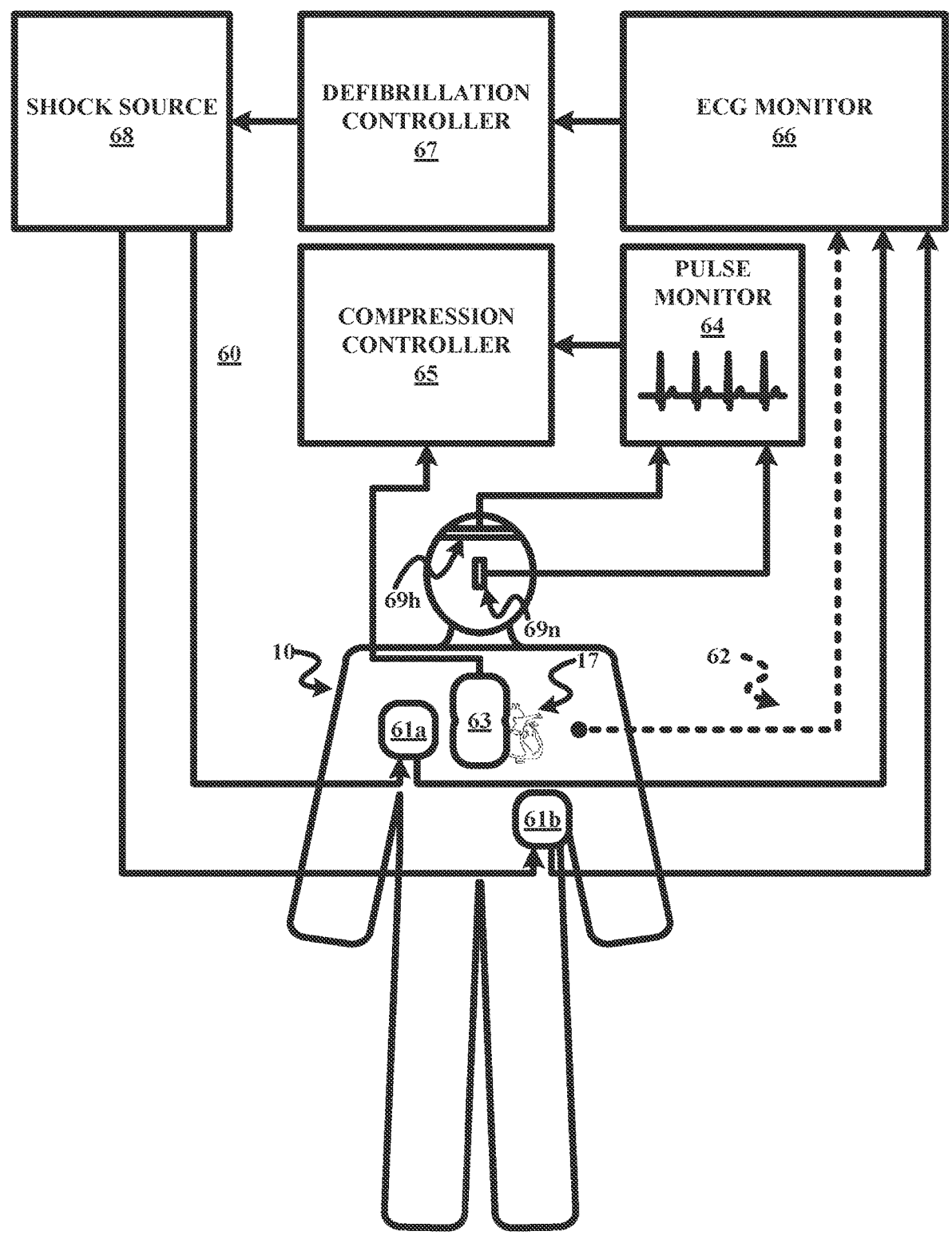
FIG. 9 illustrates an exemplary embodiment of a cardiac therapy device incorporating a heat rate monitor in accordance with the present invention.

Referring to FIG. 9, a cardiac therapy device 60 of the present invention employs a pair of electrode pads/paddles 61, optional ECG leads 62, a compression pad 63, a pulse monitor 64, a compression controller 66, an ECG monitor 66 (internal or external), a defibrillation controller 67, and a shock source 67 as known in the art.

In operation, responsive to an ECG signal from ECG monitor 66, defibrillation controller 67 controls shock source 68 in delivering a defibrillation shock via electrode pads/paddles 61 to a heart 17 of patient 10 in accordance with one or more shock therapies (e., synchronized cardioversion). Additionally, responsive to a pulse signal from pulse monitor 65, compression controller 66 provides audio instructions to a user of compression pad 63 in accordance with one or more compression therapies.

As related to the pulse signal, cardiac therapy device 60 further employs a heartbeat monitor of the present invention, such as, for example, a nose clip based heartbeat monitor 69n mounted on a nose of patient 10 as shown in FIG. 9 or a headband/head strap based heartbeat monitor 69h wrapped/strapped around a head of patient 10 as shown in FIG. 9. The displays for heartbeat monitors 69n and 69h (e.g., display 45 shown in FIG. 3) are incorporated within a pulse monitor 64, and the pulse detectors for heartbeat monitors 69n and 69h (e.g., pulse detector 44 shown in FIG. 3) may also be incorporated within pulse monitor 64.

In practice, the pulse detectors (e.g., pulse detector 44 shown in FIG. 3) for heartbeat monitors 69n and 69h may concurrently or alternatively provide the pulse signal to defibrillation controller 65 and/or compression controller 66.

Also practice, monitors 64 and 66 may be combined and/or controllers 65 and 67 may be combined.

Referring to FIGS. 2-9, those having ordinary skill in the art will appreciate numerous benefits of the present invention including, but not limited to, a simple to use, noninvasive and reliable pulse detection, particularly in emergency care for triage and guidance of therapy.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A method for a pulse detection of a person by a heart rate monitor including a plurality of multi-axis accelerometers adjoined to a platform at different angular orientations with respect to each other, each multi-axis accelerometer having acceleration sensing axes including a vertical axis and at least one of a lateral axis and a longitudinal axis, the method comprising:
   spatially mounting, via the platform, the multi-axis accelerometers at the different angular orientations of the multi-axis accelerometers with respect to each other on respective opposing body surfaces of the person, wherein the relative angular orientation of the accelerometers is rigidly maintained by the body surfaces;
   generating, via the multi-axis accelerometers as mounted on the person, differential mode signals indicative of a sensing by the multi-axis accelerometers of a physiological motion of the person relative to the vertical axes of the multi-axis accelerometers normal to a body surface of the person;
   generating, via the multi-axis accelerometers as mounted on the person, common mode signals indicative of a sensing by the multi-axis accelerometers of an extraneous motion by the person relative to the at least one of the lateral axes and the longitudinal axes of the multi-axis accelerometers parallel to the body surface of the person;
   aligning, via the heart rate monitor, the vertical axes of the multi-axis accelerometers relative to an additional baseline axis to combine the differential mode signals and cancel the common mode signals; and
   generating, via the heart rate monitor, a pulse signal from the combining of the differential mode signals and the cancelling of the common mode signals as a function of the alignment of the vertical axes of the multi-axis accelerometers.

2. The method of claim 1, wherein the platform is one of a nose clip, a headband or a head strap.

3. The method of claim 1, further comprising:
  displaying, via a display, a pulse of the person responsive to the pulse signal.

4. The method of claim 1,
  wherein the vertical axis of each multi-axis accelerometer is normal to the platform; and
  wherein the at least one the lateral axis and the longitudinal axis is parallel to the platform.

5. A heart rate monitor for detecting a pulse of a person, the heart rate monitor comprising:
  a platform;
  a plurality of multi-axis accelerometers adjoined to the platform and having different angular orientations at opposing body surfaces, each of the multi-axis accelerometers having a vertical axis to generate a respective differential mode signal indicative of a sensing by the multi-axis accelerometers of a physiological motion normal to a body surface of the person and a longitudinal axis and a lateral axis parallel to the body surface to generate common mode signals indicative of a sensing by the multi-axis accelerometers of an extraneous motion by the person relative to the at least one of the lateral axes and the longitudinal axes of the multi-axis accelerometers, wherein, in use, the relative angular orientation of the multi-axis accelerometers is rigidly maintained by the body surfaces; and
  a pulse detector operably connected to the multi-axis accelerometers to generate a pulse signal as a function of an alignment of the vertical acceleration sensing axes combining the differential mode signals and cancelling the common mode signals.

6. The heart rate monitor of claim 5,
  wherein the platform is one of a nose clip, a headband or a head strap.

7. The heart rate monitor of claim 5, further comprising:
  a display operably connected to the pulse detector to display the pulse of the person responsive to the pulse signal.

8. The heart rate monitor of claim 5,
  wherein the vertical axis of each multi-axis accelerometer is normal to the platform; and
  wherein the at least one the lateral axis and the longitudinal axis is parallel to the platform.

9. A cardiac therapy device, comprising:
  a heart rate monitor according to claim 5; and
  a pulse monitor operably connected to the pulse detector to monitor the pulse of the person responsive to the pulse signal.

10. The cardiac therapy device of claim 9, wherein the platform is one of a nose clip, a headband or a head strap.

11. The cardiac therapy device of claim 9, further comprising:
  a display operably connected to the pulse detector to display the pulse of the person responsive to the pulse signal.

12. The cardiac therapy device of claim 11, wherein the pulse monitor incorporates the display.

13. The cardiac therapy device of claim 9,
  wherein the vertical axis of each multi-axis accelerometer is normal to the platform; and
  wherein the at least one the lateral axis and the longitudinal axis is parallel to the platform.

\* \* \* \* \*